United States Patent
Swinney (10) Patent No.: US 9,433,474 B2
(45) Date of Patent: Sep. 6, 2016

(54) SYSTEM FOR DECONTAMINATING MEDICAL EQUIPMENT ITEMS AND TRACKING DECONTAMINATION PROCESS

(71) Applicant: Tristel PLC, Cambridgeshire (GB)

(72) Inventor: Paul Swinney, Cambridgeshire (GB)

(73) Assignee: Tristel PLC, Cambridgeshire (GB)

( * ) Notice: Subject to any disclaimer, the term of this patent is extended or adjusted under 35 U.S.C. 154(b) by 0 days.

(21) Appl. No.: 14/910,184

(22) PCT Filed: Sep. 10, 2014

(86) PCT No.: PCT/GB2014/052743
§ 371 (c)(1),
(2) Date: Feb. 4, 2016

(87) PCT Pub. No.: WO2015/040366
PCT Pub. Date: Mar. 26, 2015

(65) Prior Publication Data
US 2016/0175066 A1  Jun. 23, 2016

(30) Foreign Application Priority Data

Sep. 17, 2013  (GB) .................................... 1316519.6

(51) Int. Cl.
*A61B 90/70* (2016.01)
*A61L 2/18* (2006.01)
(Continued)

(52) U.S. Cl.
CPC .............. *A61B 90/70* (2016.02); *A61B 90/96* (2016.02); *A61L 2/18* (2013.01); *C11D 11/0041* (2013.01);
(Continued)

(58) Field of Classification Search
CPC ................................ A61L 2/18; A61B 90/70
USPC ............................................ 422/29, 37, 292
See application file for complete search history.

(56) References Cited

U.S. PATENT DOCUMENTS

| 2006/0051266 A1 | 3/2006 | Green et al. |
| 2011/0076192 A1 | 3/2011 | Robitaille et al. |
| 2013/0115132 A1 | 5/2013 | Engimann |

FOREIGN PATENT DOCUMENTS

| AU | 731352 B | 10/1998 |
| EP | 2073188 A1 | 3/2010 |

(Continued)

*Primary Examiner* — Sean E Conley
(74) *Attorney, Agent, or Firm* — Hayes Soloway PC (57) ABSTRACT

A decontamination system (2) suitable for cleaning and disinfecting a medical instrument (26) such as an endoscope, the system comprising: (I) a plurality of pre-clean wipes for wiping an instrument to be decontaminated each pre-clean wipe comprising a moist fabric member in its own sealed container (4); (II) a two-part disinfectant system comprising: (a) a first part comprising a first reagent in a carrier medium; and (b) a second part which is miscible with the first part and which comprises a second reagent in a carrier medium; wherein the first reagent and the second reagent will react when mixed to provide a disinfecting composition; the first part being contained in a dispenser (6) whereby it will be dispensed as a fluid when the dispenser is actuated, and the second part being absorbed or impregnated in a plurality of disinfecting wipes (30) each of which comprises a fabric member (30) in its own sealed container (8); and (III) a plurality of rinse wipes, each rinse wipe comprising a moist, sterile, fabric member in its own sealed container (10); characterized in that each pre-clean wipe container (4) is provided with a machine-readable Pre-Clean Wipe data carrier (36) which includes data specific to the pre-clean wipe; the dispenser (6) is provided with a machine-readable Dispenser data carrier (58) which includes data specific to the first part; each disinfecting wipe container (8) is provided with a machine-readable Disinfecting Wipe data carrier (44) which includes data specific to the disinfecting wipe (30); and each rinse wipe container (10) is provided with a machine-readable Rinse Wipe data carrier (50) which includes data specific to the rinse wipe.

10 Claims, 6 Drawing Sheets

(51) Int. Cl.
    *C11D 17/04*     (2006.01)
    *D21H 21/36*     (2006.01)
    *G06Q 50/22*     (2012.01)
    *C11D 11/00*     (2006.01)
    *A61L 2/28*     (2006.01)

(52) U.S. Cl.
    CPC ............. C11D 17/049 (2013.01); D21H 21/36 (2013.01); G06Q 50/22 (2013.01); *A61B 2090/701* (2016.02); *A61L 2/28* (2013.01); *A61L 2202/14* (2013.01); *A61L 2202/17* (2013.01); *A61L 2202/24* (2013.01)

(56) References Cited

FOREIGN PATENT DOCUMENTS

| | | |
|---|---|---|
| WO | 0110476 A1 | 2/2001 |
| WO | 2005107823 A1 | 11/2005 |
| WO | 2010134826 A1 | 11/2010 |

SYSTEM FOR DECONTAMINATING MEDICAL EQUIPMENT ITEMS AND TRACKING DECONTAMINATION PROCESS

FIELD OF THE INVENTION

The present invention relates to a decontamination system for ensuring that the exterior surface of a medical instrument such as an endoscope is made safe after use on one patient prior to use on another patient.

BACKGROUND TO THE INVENTION

"Traditionally, the word 'decontamination' has been applied to those cleaning procedures—automatic and/or manual—that take place prior to sterilisation. Recent documentation, however, has redefined the word to apply to the whole series of procedures to ensure that a device is made safe after use on one patient prior to use on a second. Decontamination can thus include cleaning, disinfecting and sterilising." This statement is taken from an article published in the ISSM (Institute of Sterile Service Managers) Journal, Vol. 5, No. 1 July-September 2000. The statement helps to explain what the decontamination process has come to mean in modern UK hospitals and goes on to refer to HTM2030, which has been the driver for change in processing many types of medical instruments. The term 'decontamination' will be used herein to refer to the above redefinition, including cleaning and disinfecting.

Health Technical Memorandum (HTM) 2030 was introduced in 1993 and updated in 1997 and 2001 to improve the sterile processing performance of washer disinfectors. HTM2030 addresses the use of washer-disinfectors for instruments, many of which cannot be autoclaved, for example flexible endoscopes. In essence, it describes the need to wash instruments thoroughly before disinfection/sterilisation (by heat or by chemical); to be followed by the disinfection/sterilisation stage and to culminate, in the case of chemical disinfection, in the rinsing of the instrument. HTM2030 also addresses the need for the entire process to be recorded in a traceability and audit system.

Two-part disinfecting solutions are used in applications where the active disinfecting ingredient is unstable over time. The solution is therefore prepared in situ shortly before it is to be used. A particularly important disinfecting agent is chlorine dioxide ($ClO_2$) which may be formed from mixtures of various reagents including: chlorite and acid; chlorate, peroxide and acid; and chlorite, hypochlorite, and a suitable buffer. Chlorine dioxide has excellent disinfecting and bactericidal properties, and oral ingestion in man and animals has been shown to be relatively safe.

It is not always convenient to mix up batches of solutions for use in disinfecting equipment. For wiping down (rather than thoroughly cleaning inside and out) of endoscopes and probes, wipes of alcohol, general-purpose detergent, or soapy water are generally used, but these are not as effective as chlorine dioxide. It is desirable to be able readily to make up small quantities of two-component disinfecting agents when desired and to be able to make such agents up in a form in which they may be readily handled for a particular application. It is particularly desired to provide a decontamination system which meets the HTM2030 standard.

The decontamination of endoscopes and other medical equipment to HTM2030 standard with chlorine dioxide or other suitable two-part disinfectant solutions is known. See, for example, EP 1 742 672 and U.S. Pat. No. 7,807,118, which disclose a system comprising a plurality of pre-clean wipes, a two-part disinfectant system of reagents that react when combined to provide a disinfecting composition in a fabric member, and a plurality of rinse wipes. An operator cleans an instrument with a pre-clean wipe to remove gross contamination, then disinfects the external surfaces using the freshly-prepared disinfectant wipe, and removes or neutralises the disinfectant with a rinse wipe. The system can include removable adhesive labels associated with each disinfecting wipe, which provide information about an item such as the lot or batch number, date of manufacture, or a use-by or expiry date. The adhesive labels are affixed to a space in a record sheet for recording details about the decontamination of a particular instrument, and the record sheet provides space for recordal of details such as whether the instrument is to be returned to a specific patient or to storage, and confirmation that the system components have been used in the correct order. The system aids the provision of a quality audit trail for a decontaminated medical instrument.

SUMMARY OF THE INVENTION

According to the present invention there is provided a decontamination system as specified in claim 1. Preferred features are specified in the dependent claims.

The system renders paper trails obsolete and reduces the risk of error, either through incorrect manual recording of data or accidental use of the system components in the wrong order. Preferred embodiments provide for important information to be recorded relating to the operators of the system, for example nursing or hospital staff, the instrument being decontaminated, and patient details. The system can provide for pre-authorisation for a particular instrument to be decontaminated, optionally with specified decontamination system components and/or a specified operator.

It will be appreciated that any suitable machine-readable data carriers may be employed in the invention. Examples are bar codes and RFID tags, together with appropriate readers. The invention will, for convenience, be illustrated with reference to the use of bar codes and a bar code reader; however, it will be understood that the invention is not limited to this embodiment.

The pre-clean wipes, the two-part disinfectant system, the rinse wipes and the individual sealed containers such as sachets, may each be as described and discussed in EP 1 742 672 and U.S. Pat. No. 7,807,118 the contents and experimental results of which are, for brevity, hereby incorporated by reference in their entirety.

BRIEF DESCRIPTION OF THE DRAWINGS

The invention will now be further described, by way of example, with reference to the following drawings in which.

DETAILED DESCRIPTION

Figure 1:
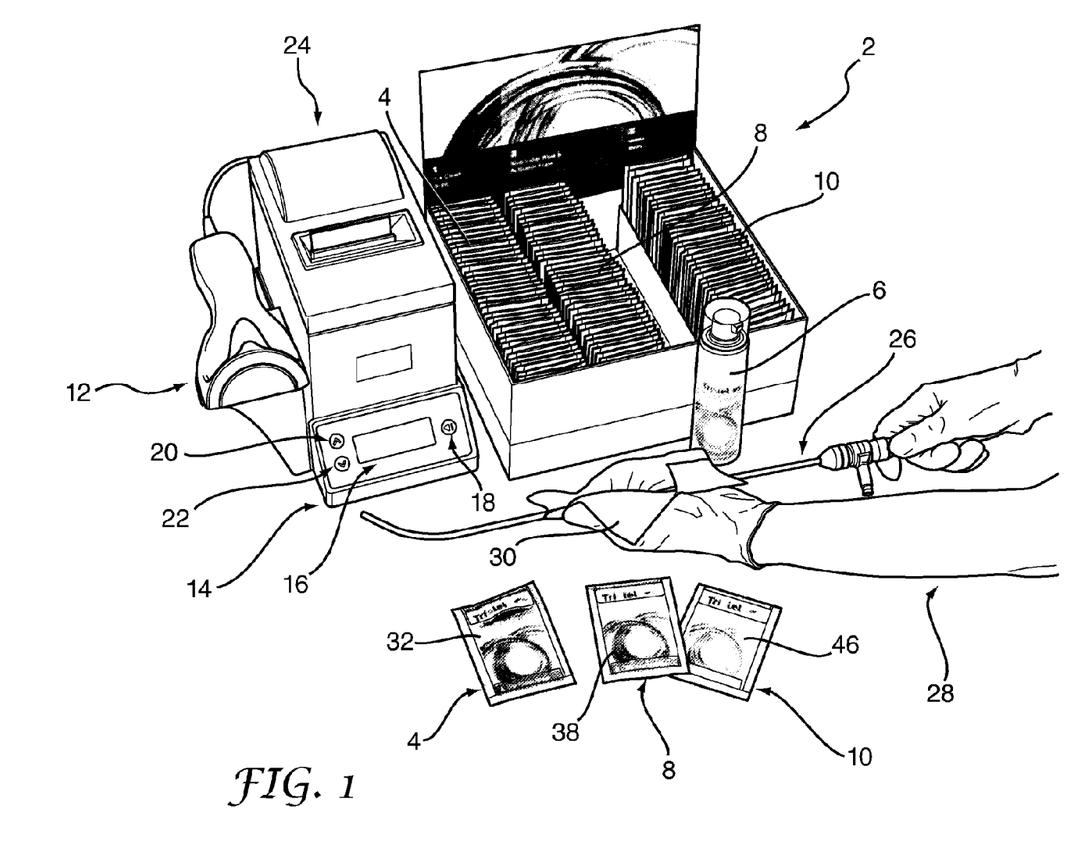
FIG. 1 shows a decontamination system in accordance with an embodiment of the present invention, being used for decontamination of an instrument.

The decontamination system 2 shown in FIG. 1 in this embodiment comprises a box which contains a plurality of containers 4,8,10 and a dispenser 6. Each container in this example is a sachet which is sealed and contains a fabric wipe for a specified purpose. The sachets 4,8,10 contain, respectively, a pre-clean wipe, a disinfecting wipe and a rinse wipe. The dispenser 6 (best shown in FIG. 5) contains a first part comprising a first reagent in a carrier medium. The first reagent and carrier medium are dispensed as a metered dose via a nozzle 54 when a trigger 52 is depressed. A cap 56 covers the nozzle 54 when not in use. The dispenser is provided with a Dispenser data carrier 58 in the form of a bar code which is printed on or adhered to a surface of the dispenser. The Dispenser data carrier contains encoded data relating to the first part, which optionally includes its lot or batch number, date of manufacture, use-by or expiry date, or any other relevant information.

Figure 5:
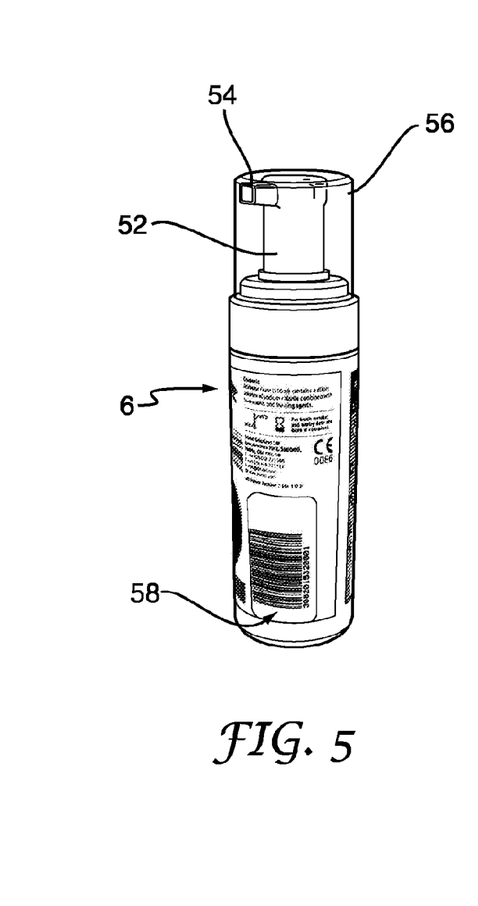
FIG. 5 is a view of the pump dispenser from the system of FIG. 1.
Figure 6:
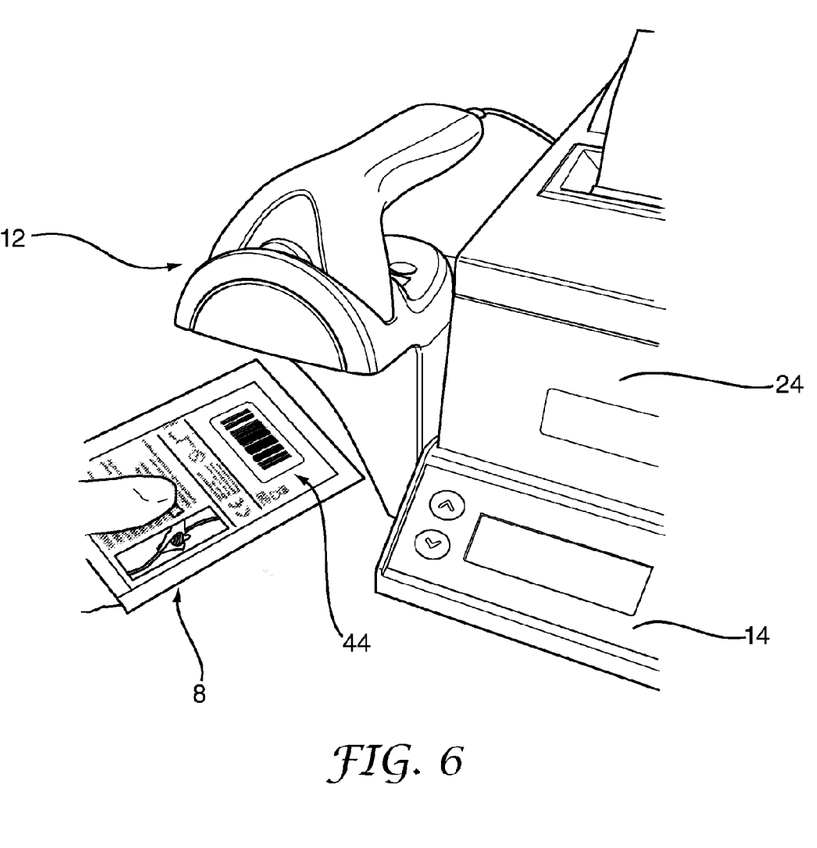
FIG. 6 shows a stage in the use of the decontamination system of FIG. 1.

In the present example, the first part is a liquid comprising 0.75% of a first reagent (sodium chlorite), 3.0% foam promoter (Cocamidopropyl Betaine). The remainder is deionised water. In this specification, all parts are by weight unless otherwise indicated. Operation of the trigger 52 dispenses the first part as a foam.

Figure 2:
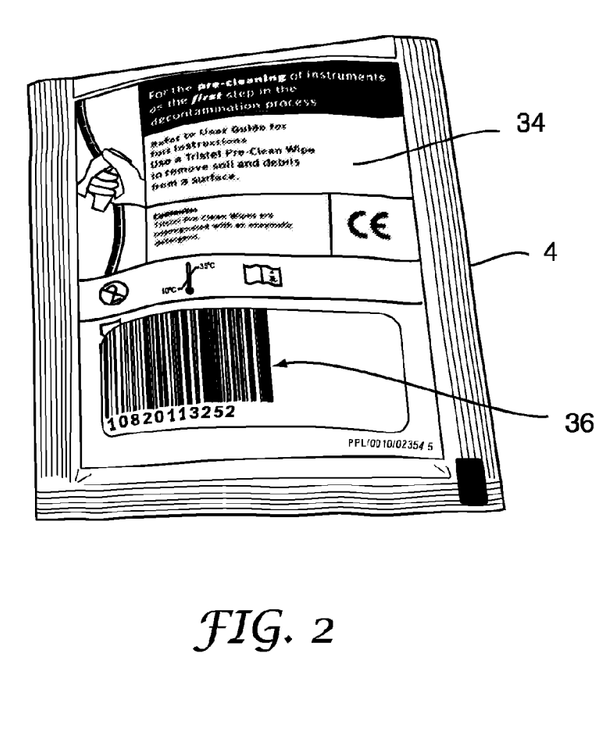
FIGS. 2 to 4 illustrate sachets from the system of FIG. 1.
Figure 3:
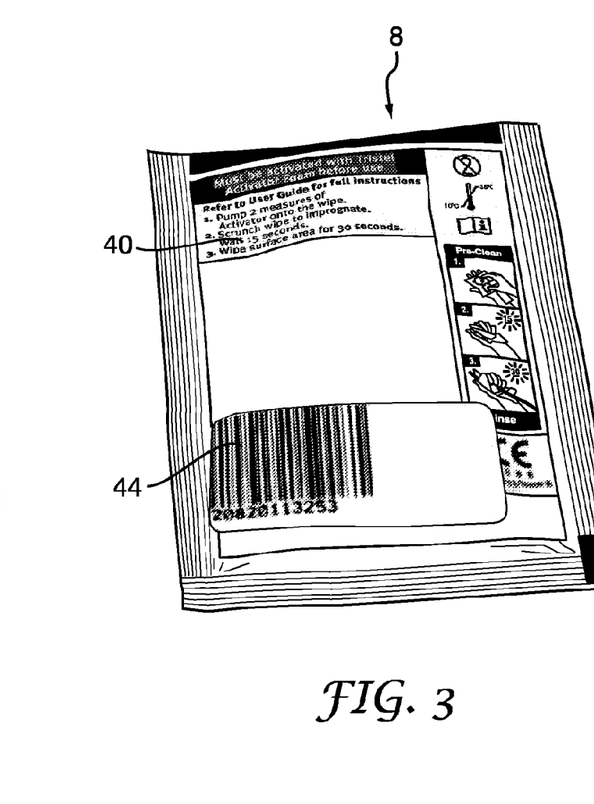
Figure 4:
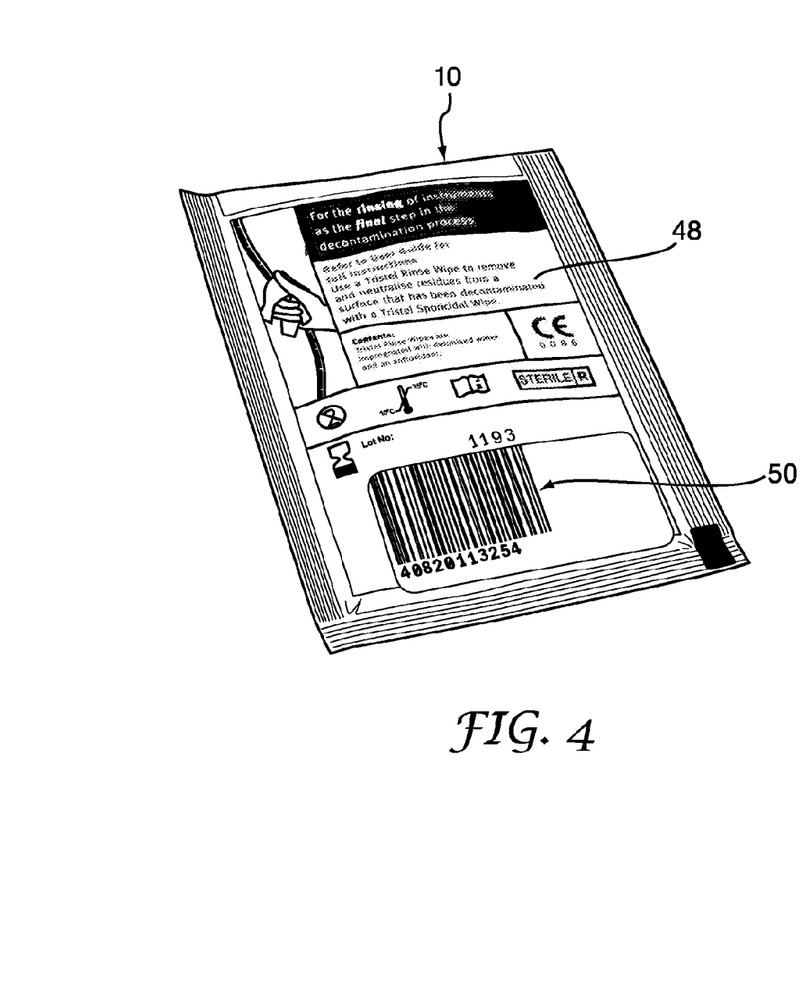

The sachets 4,8,10 each have respective front labels 32,38,46 which identify their function to a operator, and respective back labels 34,40,48 (FIGS. 2-4) which display operator instructions and information about lot numbers and expiry dates. Each pre-clean wipe sachet 4 carries a Pre-clean data carrier 36, each disinfecting wipe sachet 8 carries a Disinfecting Wipe data carrier 44 and each rinse wipe sachet 10 carries a Rinse Wipe data carrier 50. The various data carriers each contain encoded data relating to the content of the sachet with which they are associated, which optionally includes its lot or batch number, date of manufacture, use-by or expiry date, or any other relevant information. In the present examples, the bar codes are all Code 128 codes. Each sachet and the dispenser bar codes comprise the sequence number, the month and year (expiry date) and batch number.

In this example, the disinfecting wipes 30 are impregnated with an aqueous acid solution (second part) which comprises 0.5% citric acid, 0.05% sorbic acid, 0.05% boric acid. The solution also comprises 0.35% of a buffer (trisodium phosphate). The solution also comprises 0.25% trisodium citrate, 1.0% glycerine, 0.1% benzotriazole, 0.1% sodium molybdate and 0.3% sodium nitrate. The remainder is deionised water.

The pump dispenser 6 and disinfecting wipe sachets 8 together comprise the disinfectant system. To activate a disinfecting wipe, a operator removes the wipe 30 from the container 8, and applies a portion of foam from the dispenser 6 to the wipe 30. To facilitate mixing of the reagents in the foam and the wipe, the operator may fold the wipe in half and crush or rub the folded wipe before opening it out. Preferably, one of the components is provided with a pH-sensitive indicator which changes colour or becomes coloured when adequate mixing has occurred, thereby indicating that sufficient $ClO_2$ has been generated in the wipe.

Once the disinfecting wipe has been activated, it is ready to be used for disinfecting a medical instrument 26 such as an endoscope 26 after the instrument has been cleaned using a pre-clean wipe in accordance with operator instructions.

After the external surfaces of the instrument have been disinfected, a operator 28 wipes the external surfaces with a rinse wipe in accordance with operator instructions, leaving the instrument 26 clean and disinfected, and safe for use with another patient.

Each sachet 4,8,10 is factory-sealed and may be disposed of after the wipe has been removed.

In this example, the pre-clean wipes contain the fluid formulation set forth in Table 1.

TABLE 1

| Ingredients | % w/w | CAS No. |
| --- | --- | --- |
| Deionised water | 93.285 | 7732-18-5 |
| Trisodium citrate | 0.5 | 68-04-02 |
| Sodium benzoate | 0.2 | 532-32-1 |
| Isopropanol | 1.5 | 67-63-0 |
| Monopropylene glycol | 3.0 | 57-55-06 |
| Glycol ethers (Downal DDNP grade) | 1.0 | 029911-27-1 |
| Alcalase | 0.2 | 9014-01-1 |
| Termamyl | 0.02 | 9000-90-2 |
| Lipolase | 0.02 | 9001-61-1 |
| Surfactant LF6 (low-foam) | 0.1 | 107600-33-9 |
| Phenoxyethanol (preservative) | 0.15 | 26172-55-4 |
| Silicone emulsion (antifoamer) | 0.025 | |

The trisodium citrate functions as a buffer; sodium benzoate functions as a preservative and corrosion inhibitor; monopropylene glycol functions as a humectant and solubiliser; the enzymes promote digestion and solubilizing of organic deposits.

The fluid formulation for the rinse wipes is given in Table 2.

TABLE 2

| RINSE WIPE FORMULATION | | |
| --- | --- | --- |
| Ingredients | % w/w | CAS No. |
| Deionised water | 97.25 | 7732-18-5 |
| Sodium thiosulphate | 0.5 | 7772-98-7 |
| EDTA (sodium salt) | 0.1 | 139-33-3 |
| Silicone emulsion (Dow 365) | 2.0 | |
| Phenoxyethanol (preservative) | 0.15 | 26172-55-4 |

In the illustrated embodiment, the system includes a bar code reader 12 for reading data from the bar codes on the sachets and the dispenser, and optionally bar codes relating to a patient, an instrument 26 to be decontaminated, and/or the operator 28 of the system. The reader 12 is operationally connected to an electronic controller 14 which has means for providing visual and/or audible information to the operator 28. In this example, the controller 14 has a display 16. The controller has control buttons 18,20,22 for a operator 28 to set various parameters and navigate menus. The controller 14 in this example communicates with a printer 24 for printing out various information tickets.

Some hospitals use data carriers such as bar codes to identify their patients, whilst other hospitals do not. When the system is set up, the operator determines whether the controller 14 should prompt for a Patient bar code to be scanned or not. If not, then the first prompt is for the Instrument bar code to be scanned. If the hospital has Patient bar codes, then the controller 14 will prompt for this and the reader 12 can scan them. The second prompt will then be for the instrument to be scanned. Typically, Patient bar codes will be kept in the patient record book at the hospital. A benefit of using bar codes as data carriers, rather than RFID tags, is that errors resulting from inadvertent data entry from two Patient data carriers that are close together are reduced or eliminated. Whereas a specific bar code can be unambiguously read, if two RFID tags are close together in a book, one may be read by a tag reader instead of another when proximity but not contact is sufficient for a reading to be taken.

Figure 7:
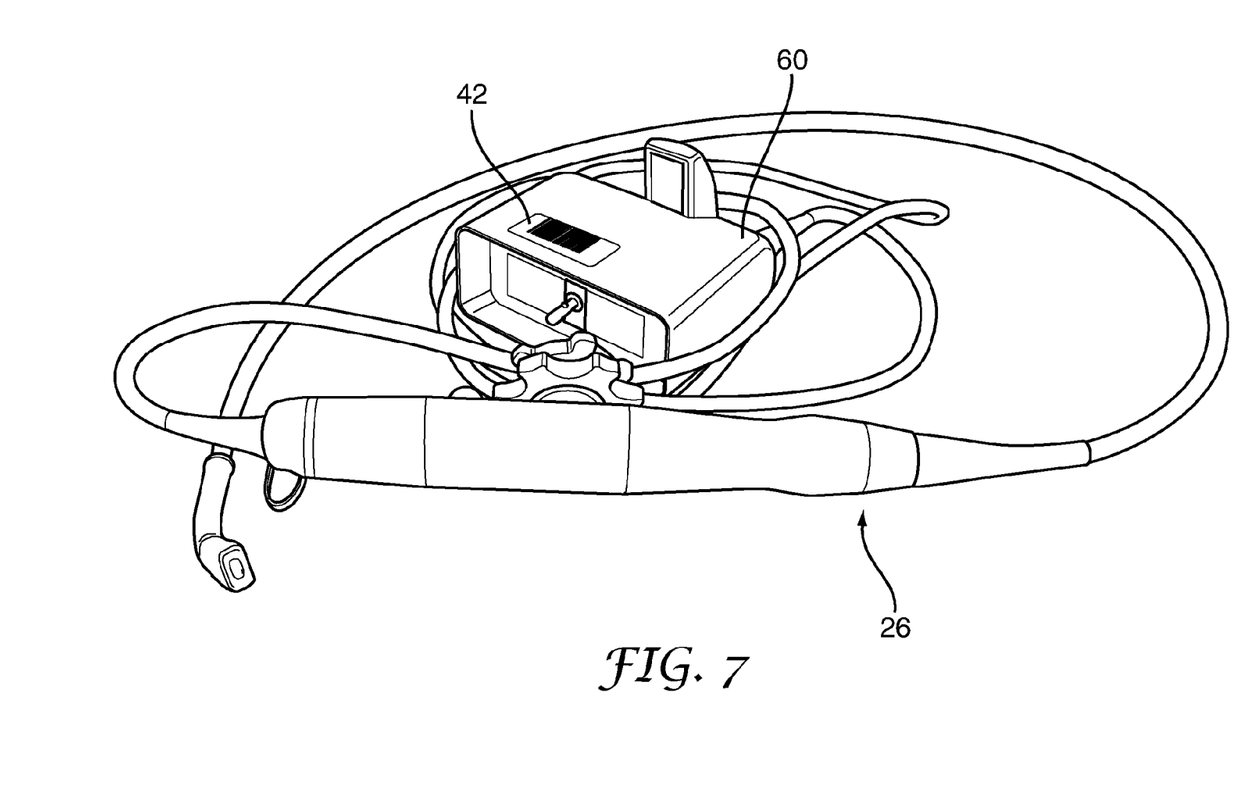
FIGS. 7 and 8 illustrate respectively an instrument with bar code and an operator badge with a bar code for use in embodiments of the invention.
Figure 8:
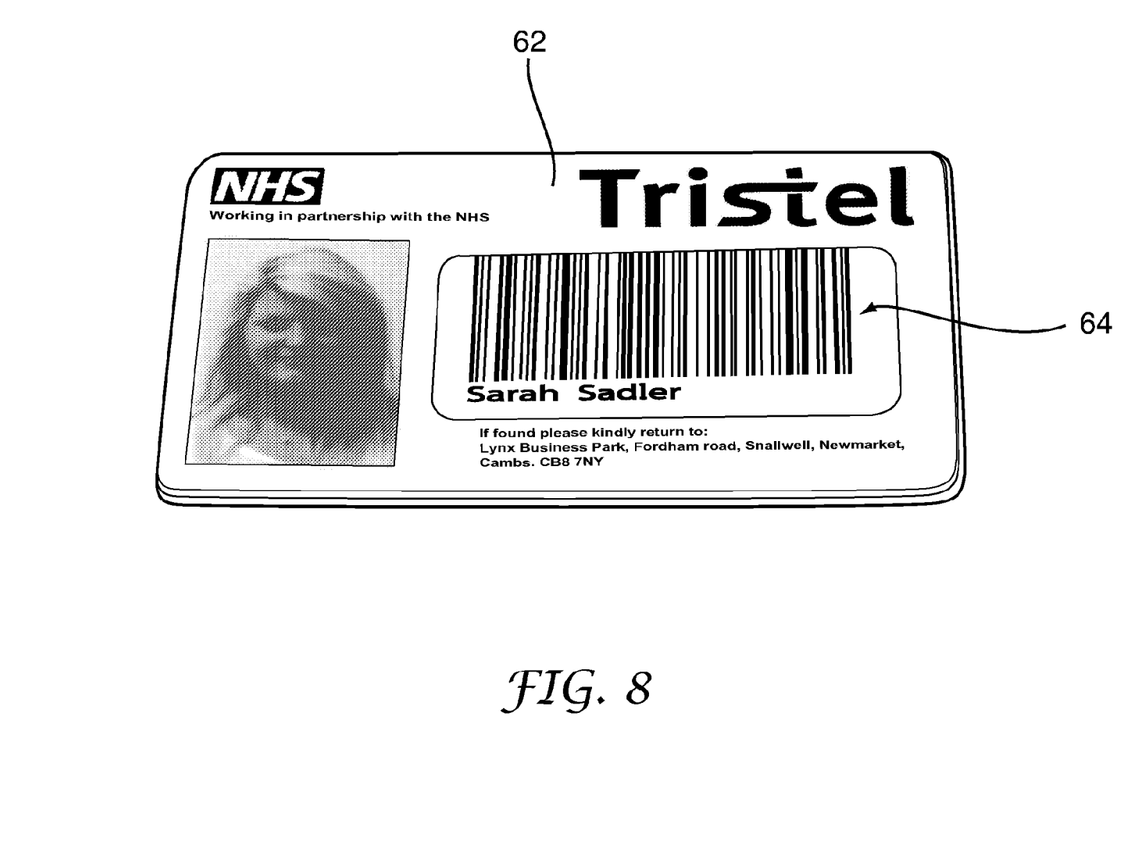

Operator bar codes 64 are supplied to suitably-trained staff and may be worn for example on a nurse's badge 62 or lanyard, as illustrated in FIG. 8. Instrument bar codes 42 are applied only to instruments 26 suitable to be decontaminated by means of the present system and are typically affixed to the instrument itself or an associated item of equipment; the optimum location will vary for different types of instrument. Referring to FIG. 7, the Instrument bar code 42 is affixed to a light source/viewer 60 which is attached to an endoscope. These bar codes are printed on resistant material to prevent or inhibit them from getting scratched, falling off or being negatively affected by liquids.

During normal operation, the controller 14 in this example will prompt for scans in the following order. At each point, the appropriate bar code is to be held underneath the reader. A bleep will confirm the scan was completed and the controller will prompt for the next stage.

Bar codes are requested in the following order:
1. Patient (if enabled in set-up)
2. Instrument
3. Pre-Clean Wipe
4. Disinfecting Wipe
5. Activator Foam (Dispenser)
6. Rinse Wpe
7. Operator The controller will detect if the wipes are not scanned in their correct sequence or if the incorrect product is scanned. For example:

The operator scans the Instrument bar code followed by the Dispenser (Activator Foam) bar code. An error bleep will sound and the display 16 will show "Incorrect product". The cycle will need to be restarted by pressing button 18.

The operator scans the Instrument followed by an expired Pre-Clean Wipe. An error bleep will sound and the display 16 will show "Expired product". The cycle will need to be restarted by pressing button 18.

If all scans are correct, the controller 14 will cause the printer 24 to print out a ticket (the Trace Ticket) and show the completed timestamp on the display screen 16. If within 30 seconds button 20 is pressed, a second ticket will be printed: the Patient Ticket. This is intended to be a copy for the patient notes. The operator is instructed to tear off the Trace Ticket before pressing button 20 for the Patient Ticket. Button 20 can be pressed multiple times if more than two copies are required but only the Patient Ticket will be printed. The system in this embodiment provides that there can only be one copy of the Trace Ticket.

In an alternative embodiment, the printer is substituted by a power supply, cable or other means for connection to a PC or other external computer apparatus, and software installation CD or other data transfer means. The operator installs the software and connects the controller to the external computer. In one embodiment, the software constantly runs and monitors for incoming scan results. Once the software has been configured correctly, logging will happen in the background without user intervention.

Example user instructions are given below.
Using Tristel™ Trio Trace™
Step 1:
Pre-Clean Wipe The first step in the decontamination process of medical devices is the thorough pre-cleaning of the surface to remove soil and organic matter prior to high level disinfection. The Pre-Clean Wipe is impregnated with a low-foaming surfactant system combined with triple enzymes, producing ultra-low surface tension for rapid cleaning. It is an effective means of performing the pre-cleaning stage of the decontamination process.

The Pre-Clean Wipe is a Class I Medical Device carrying the CE mark in accordance with the European Medical Device Directive 93/42/EEC and the 2007/47/EC amendments thereto.

Do not use if the Pre-Clean Wipe sachet has been damaged.
   Leave the Trace Scanner (bar code reader) placed in the cradle during the entire decontamination process for hands free operation.

1. Disinfect hands and wear gloves when handling disinfectants and medical devices.
2. If Enabled in set-up, scan the Patient bar code. A beep will sound and Trace Scanner will light up green when the scan is successful.
3. Scan the instrument bar code. A beep will sound and Trace Scanner will light up green when the scan is successful.
4. Take one Pre-Clean Wipe sachet and scan the bar code on the back of the sachet. A beep will sound and Trace Scanner will light up green when the scan is successful.
5. Tear the sachet, remove the wipe, unfold it and lay out on the palm of your hand.
6. Unfold the wipe and lay out on the palm of your hand.
7. Thoroughly wipe the surface of the medical device until soil and organic matter have been visibly removed. (In case of heavy soiling more than one wipe may have to be used).
8. Place the instrument back into the dirty area.
9. Discard the wipe and gloves to clinical waste.

Step 2:
Sporicidal Wipe (Disinfecting Wipe)

The second step in the decontamination process is the high level disinfection of the medical device.

The Sporicidal Wipe incorporates Tristel's patented chlorine dioxide ($ClO_2$) chemistry. It can kill all organisms, including spores, on a pre-cleaned medical device with a contact time of only 30 seconds. Examples of instruments that can be disinfected with the Sporicidal Wipe are nasendoscopes, transoesophageal ecocardio probes, transvaginal and transrectal ultrasound probes, and GI manometry catheters.

The Sporicidal Wipe is only for use on non-lumened heat sensitive, re-useable medical devices.
   Do not use if the sachet and/or Activator Foam bottle have been damaged.
   Pre-clean the surface of the medical device before using the Sporicidal Wipe. As with all decontamination processes, thorough pre-cleaning of the surface to remove soil and organic matter is an essential first step. Tristel recommends the use of the Pre-Clean Wipe prior to disinfecting with the Sporicidal Wipe.

The Sporicidal Wipe is a Class IIb medical device carrying the CE mark in accordance with the European Medical Device Directive 93/42/EEC and the 2007/47/EC amendments thereto.

10. Disinfect hands and wear new gloves.
11. Take a Sporicidal Wipe sachet and scan the bar code on the back of the sachet.
12. Scan the Activator Foam bottle bar code.
13. Tear the sachet, remove the wipe, unfold it and lay out on the palm of your hand.
14. Take the lid off the Activator Foam bottle. If the Activator Foam bottle is being used for the first time, depress the pump two to four times to prime the foamer. The first output from the foam bottle can be left on the wipe, to be followed by two complete pumps. The Activator Foam bottle is then primed for subsequent wipes. For all subsequent wipes, pump two measures of Activator Foam onto the Sporicidal Wipe.

15. Scrunch together 15 seconds to activate. Ensure that the wipe is evenly covered with foam. Presence of 'chlorine like' odour confirms that the wipe is ready to use.

16. Wipe the surface of the medical device until it has been covered with the disinfecting preparation.

17. Once the entire surface has been wiped and covered with the disinfecting preparation, place the instrument in the clean area and wait 30 seconds.

18. Dispose of the wipe to clinical waste.

Remember:
Activate the wipe as soon as you have removed it from the sachet and use it immediately.
An activated wipe will have a faint odour of $ClO_2$.
Rinse the surface after use of the Sporicidal Wipe.

Step 3:
Rinse Wipe

The final step in the decontamination process is the rinsing of the surface that has been treated by a chemical biocide. The Rinse Wipe is impregnated with de-ionised water and a low level of antioxidant which will remove chemical residues from a surface that has been decontaminated with the Sporicidal Wipe.

Each Rinse Wipe sachet is packed and then sterilised by gamma irradiation.

The Rinse Wipe is a Class I Sterile Device carrying the CE mark in accordance with the European Medical Device Directive 93/42/EEC and the 2007/47/EC amendments thereto.

Do not use if the Rinse Wipe sachet has been damaged.

19. Take a Rinse Wipe sachet and scan the bar code on the back of the sachet.

20. Tear the sachet, remove the wipe, unfold it and lay out on the palm of your hand.

21. Thoroughly wipe the surface of the device that has been decontaminated.

22. Discard the wipe and gloves to clinical waste.

Tristel and Trio Trace are trade marks of Tristel PLC.

Thus, the present invention provides a system for decontaminating a medical instrument such as an endoscope by cleaning, disinfecting and rinsing the external surfaces of the instrument so that it is safe after use on one patient prior to use on another patient. The system provides a manual decontamination process which in some embodiments can link to electronic patient records to provide traceability and process verifiability. Information which may be read includes the type of device to be decontaminated, its reference number, its method of decontamination, and other details including the ID number of the patient on which the device has most recently been used, the date and time of decontamination, and the identity of the operator. The electronic record permits recording of each of the pre-clean wipe process, the disinfecting process, and the rinse wipe process. It also provides information as to the immediate destination of the decontaminated item—either for use with the patient or return to storage, and can ensure that errors in the order of use of the various system components are detected, thereby reducing or eliminating operator error.

The invention claimed is:

1. A decontamination system suitable for cleaning and disinfecting a medical instrument such as an endoscope, the system comprising:

(I) a plurality of pre-clean wipes for wiping an instrument to be decontaminated each pre-clean wipe comprising a moist fabric member in its own sealed container;

(II) a two-part disinfectant system comprising:
(a) a first part comprising a first reagent in a carrier medium; and
(b) a second part which is miscible with the first part and which comprises a second reagent in a carrier medium;
wherein the first reagent and the second reagent will react when mixed to provide a disinfecting composition;
the first part contained in a dispenser whereby it will be dispensed as a fluid when the dispenser is actuated, and the second part absorbed or impregnated in a plurality of disinfecting wipes each of which comprises a fabric member in its own sealed container; and (III) a plurality of rinse wipes, each rinse wipe comprising a moist, sterile, fabric member in its own sealed container; wherein each pre-clean wipe container is provided with a machine-readable Pre-Clean Wipe data carrier which includes data specific to the pre-clean wipe;

the dispenser is provided with a machine-readable Dispenser data carrier which includes data specific to the first part;

each disinfecting wipe container is provided with a machine-readable Disinfecting Wipe data carrier which includes data specific to the disinfecting wipe; and each rinse wipe container is provided with a machine-readable Rinse Wipe data carrier which includes data specific to the rinse wipe characterised in that the system further comprises a reader for reading data from said data carriers, and an electronic controller for receiving data from the reader and providing visual and/or audible information to an operator of the system;

the controller programmed and adapted to signal an error condition if data carriers are read by the reader in an order which does not correspond to a predetermined sequence.

2. A system according to claim 1, further comprising a machine-readable Instrument data carrier containing data specific to an instrument to be decontaminated.

3. A system according to claim 1, further comprising a machine-readable Operator data carrier containing data specific to an operator of the system.

4. A system according to claim 1, further comprising a machine-readable Patient data carrier containing data specific to a patient.

5. A system according to claim 1, wherein each of the Pre-Clean Wipe data carriers, the Dispenser data carriers, the Disinfecting Wipe data carriers and the Rinse Wipe data carriers carries encoded data about the contents of its associated container or dispenser including at least one of: the lot or batch number; the date of manufacture; a use-by or expiry date.

6. A system according to claim 1, wherein each data carrier is an RFID tag.

7. A system according to claim 1, wherein each data carrier is a bar code.

8. A system according to claim 1, further comprising a printer for providing a print record relating to a decontamination cycle of an instrument, said record being derived from data received by the controller from the reader.

9. A system according to claim 1, wherein the controller is arranged and adapted to send data relating to at least a part of a decontamination cycle of an instrument to a computer database.

10. A system according to claim 1, wherein the controller is programmed and adapted to signal an error condition if an expired use-by date is detected.

\* \* \* \* \*